United States Patent [19]

Labour et al.

[11] 4,445,505
[45] May 1, 1984

[54] KNEE BRACE FOR PREVENTING LATERAL DISPLACEMENT OF THE PATELLA

[76] Inventors: Donald Labour, 82 Wellsmere Rd., Roslindale, Mass. 02167; James R. Cannon, 22 Karen Dr., Randolph, Mass. 02368; Alfred Klugman, 187 Woodward St., Newton, Mass. 02168

[21] Appl. No.: 335,197

[22] Filed: Dec. 28, 1981

[51] Int. Cl.³ ............................................. A61F 3/00
[52] U.S. Cl. .................................. 128/80 C; 128/165
[58] Field of Search .............. 128/80 C, 165, 87 R; 2/22, 24

[56] References Cited

U.S. PATENT DOCUMENTS

| | | | |
|---|---|---|---|
| 3,581,741 | 6/1971 | Rosman et al. | 128/80 C |
| 3,804,084 | 4/1974 | Lehman | 128/80 C |
| 4,084,584 | 4/1978 | Detty | 128/80 C |
| 4,201,203 | 5/1980 | Applegate | 128/80 C |
| 4,296,744 | 10/1981 | Palumbo | 128/165 |

*Primary Examiner*—John D. Yasko
*Attorney, Agent, or Firm*—Wolf, Greenfield & Sacks

[57] ABSTRACT

A knee brace for preventing lateral displacement of the patella, made of an elasticized sleeve worn over the leg and spanning the knee. The sleeve carries a pair of pads, one of which lies immediately adjacent the outer edge of the patella and blocks the patella from lateral displacement. The second pad overlies the medial femoral epicondyl to prevent the sleeve from rotating outwardly as forces are applied against the first pad by the patella. The pads are locked in place by an elastic strap secured to the sleeve and running laterally to medially over the knee.

17 Claims, 12 Drawing Figures

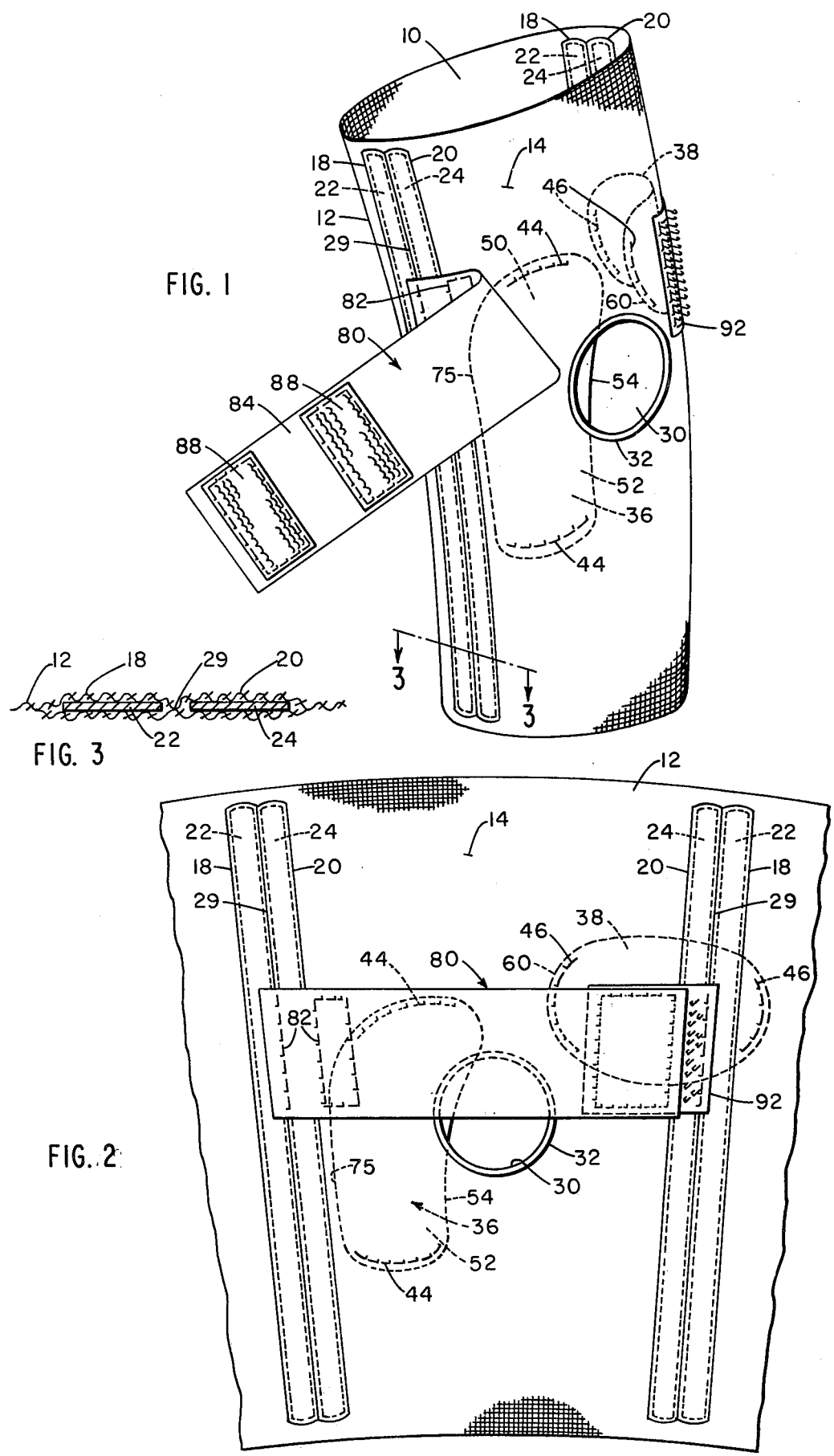

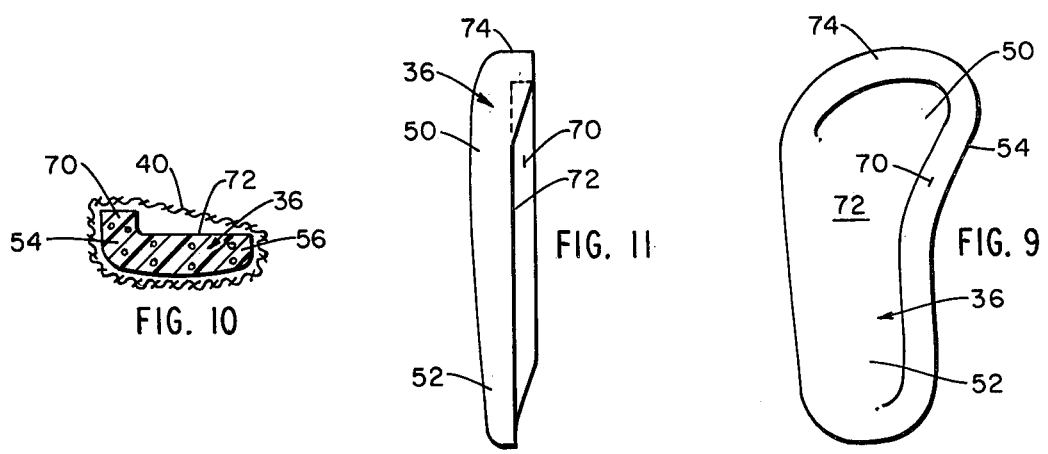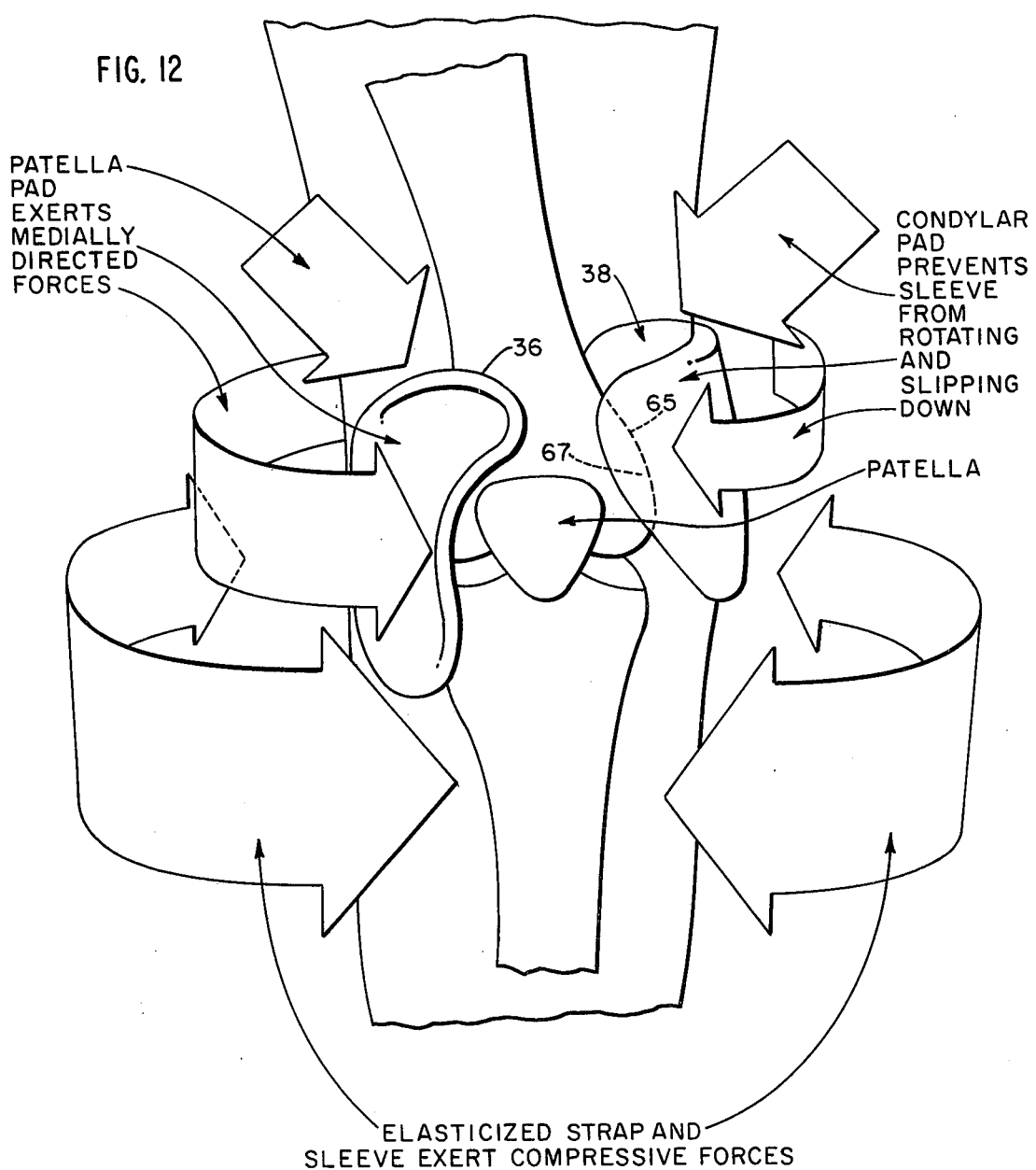

KNEE BRACE FOR PREVENTING LATERAL DISPLACEMENT OF THE PATELLA

INTRODUCTION

This invention relates to knee braces and more particularly comprises a brace for preventing lateral displacement of the patella in the femoral groove.

A variety of devices have appeared on the market to be worn about the knee to maintain patella alignment. Such devices are shown in U.S. Pat. Nos. 4,084,584; 4,201,203; 3,084,685; 4,116,236; and, 4,280,578. These and other supports and braces designed to maintain patella alignment are all entirely dependent upon the proper positioning of the device on the leg about the knee. They all include some form of pad or opening designed to engage the patella and prevent excessive lateral or medial displacement of the patella in the femoral groove. However, if the support or brace turns on the leg so as to displace the pad or opening from the patella, the device will no longer perform its intended function. None of these devices includes means which is capable of maintaining the proper position of the support or brace about the knee so that the opening or pad provided to prevent patella displacement is in position to perform its intended function.

The principal object of the present invention is to provide a knee brace that not only includes means for preventing lateral displacement of the patella, but also includes means for maintaining the brace itself in proper position on the leg.

Another important object of this invention is to provide a knee brace for preventing patella displacement, which is both comfortable when worn and does not excessively interfere with normal use of the leg.

SUMMARY OF THE INVENTION

To accomplish these and other objects, the knee brace of the present invention includes an elasticized sleeve which is generally shaped to conform to the shape of the lower thigh, knee and upper calf regions of the leg. The sleeve is stretchable both in a longitudinal and circumferential direction so as to enable the leg to bend in the normal manner without causing abrasions or irritation of the skin and without applying excessive pressures to the leg. A hole is provided in the brace, which overlies the patella when the brace is in place. Secured to the inner surface of the sleeve is a first longitudinally elongated pad (patella pad) that is positioned to lie immediately adjacent the outer edge of the patella so as to form an obstruction against its lateral displacement during the entire excursion of the patella when the knee is bent. A second pad (condylar pad) is provided on the inside of the sleeve and disposed above and to the inside of the opening. The second pad is shaped to overlie the medial epicondylar notch and form an anchor for the sleeve so as to prevent it from rotating or slipping down on the leg even when the leg is bent. The pads are made of a compliant material such as a firm polyethylene foam so that they will conform to the precise contours of the portions of the leg which they contact, but which nevertheless possess sufficient rigidity so as to perform their intended functions of preventing lateral displacement of the patella and outward rotation of the sleeve. A strap is stitched to the sleeve laterally of the first pad and carries a Velcro-type fastener which locks to a mating Velcro-type fastener over the second pad. The strap is stretchable and is intended to tighten the sleeve about the knee and thereby force the pads firmly in position.

These and other objects and features of the present invention will be better understood and appreciated from the following detailed description of one embodiment thereof, selected for purposes of illustration and shown in the accompanying drawings.

BRIEF FIGURE DESCRIPTION

FIG. 1 is a perspective view of a right knee brace of this invention, viewed from the front;

FIG. 2 is a developed view of the front of the brace of FIG. 1 viewed from the outside;

FIG. 3 is a fragmentary cross sectional view of the brace taken along section line 3—3 of FIG. 1;

Figure 4:
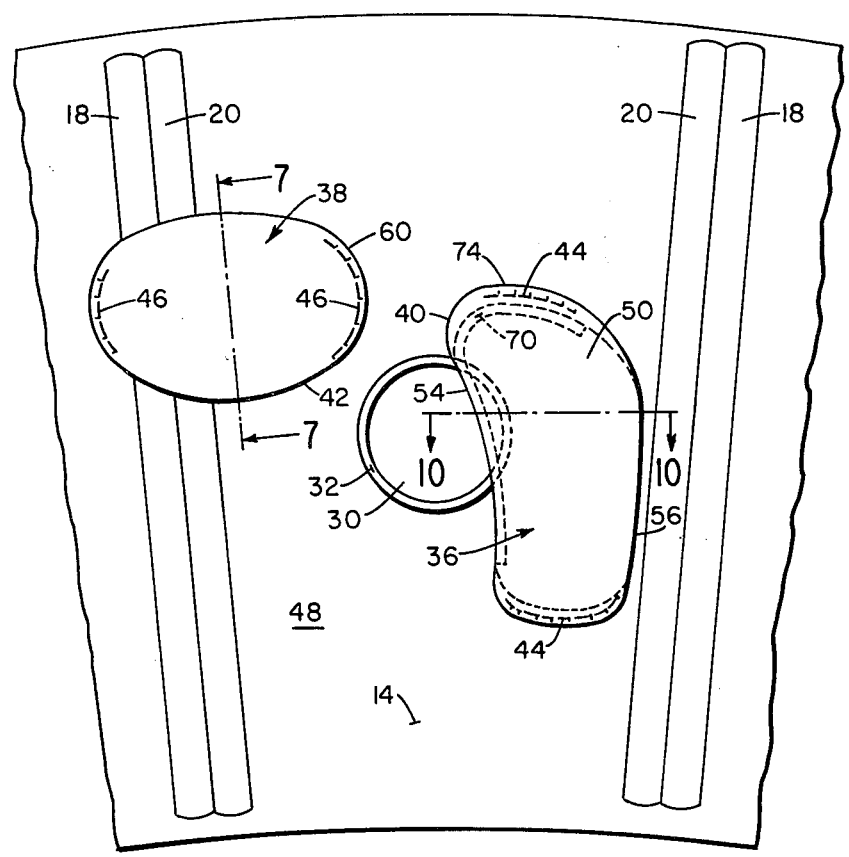
FIG. 4 is a developed view of the front of the brace of FIG. 1 viewed from the inside.
Figure 5:
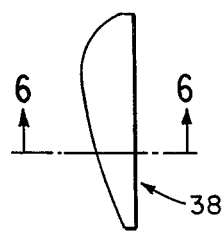
FIG. 5 is a side view of the condylar pad of the brace.
Figure 6:
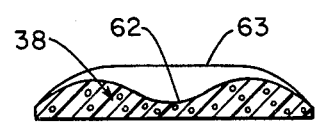
Figure 7:
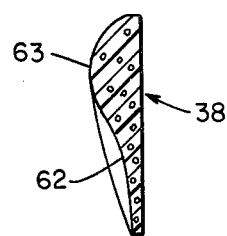
Figure 8:
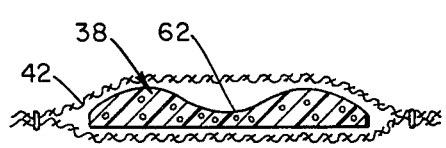

FIGS. 6 and 7 are cross sectional views of the condylar pad taken along section lines 6—6 and 7—7 in FIGS. 5 and 4, respectively;

FIG. 8 is a cross sectional view of the pad similar to FIG. 6 but showing the pad in its knitted pocket;

FIG. 9 is a detailed view of the outer face of the patella pad which prevents lateral displacement of the patella; and FIG. 10 is a cross sectional view of the patella pad within its knitted pocket taken along the section line 10—10 in FIG. 4;

FIG. 11 is a side view of the patella pad; and

FIG. 12 is a diagramatic view of the right knee and parts of the brace of the present invention in place on it and suggesting the manner in which its various components cooperate with the anatomy to perform their respective and combined functions.

DETAILED DESCRIPTION

The knee brace 10 shown in the drawings is embodied in a knitted, elasticized sleeve 12 which is worn over the knee and extends from the upper portion of the calf of the leg to the thigh. The brace shown is designed for the right leg, and a mirror image of the brace would be suitable for the left leg.

Sleeve 12 is stretchable both in a longitudinal and circumferential direction and preferably is knitted of a soft cotton yarn and elasticized thread so as to be comfortable on the body. The sleeves in an adult size may be approximately ten inches long and twelve inches in circumference at the middle. Of course the size may vary depending upon the body build of the patient to wear the device.

As shown in FIGS. 1-3, a pair of pockets 18 and 20 are knitted into the sleeve along each side of the sleeve, and stays 22 and 24 are enclosed in the pockets separated by a knitted seam 29. The stays are locked in their respective pockets and do not cross or overlap one another when the brace is worn. The stays extend substantially the full length of the sleeve and typically may be made of a spring-like material such as flat coil wire affording considerable flexibility to the brace. The principal purpose of the stays is to prevent the sleeve from curling at its upper and lower edges and from spirally twisting when the brace is worn. The stays are not intended to impede bending of the leg at the knee.

A circular opening 30 provided with a suitable binding 32 at the edge is formed substantially in the center of front portion 14 of the sleeve. The opening 30 may be approximately 2½ inches in diameter and is positioned so as to be aligned with the patella when the sleeve is worn. The opening 30 relieves pressure against the patella, prevents abrasion of the skin during vigorous activity of the patient, and increases the flexibility of the brace at the patella.

A patella pad 36 and a condylar 38 are sewn to the inside of the sleeve 12 and are generally confined to the front portion 14. Pad 36 imparts stability to the patella by preventing lateral patella displacement, and pad 38 retains the brace 10 in place on the leg and thereby maintains the proper relationship between pad 36 and the patella. It will be appreciated that if the brace twists laterally or outwardly on the patient's leg, pad 36 will move away from the patella and prevent the pad from bearing against the patella and performing its intended function.

Pads 36 and 38 are both made of a rather stiff but yieldable plastic material such as a firm polyethylene foam. The material selected should be lightweight and be sufficiently yielding so as to conform to the contours of the leg on which the sleeve is worn. Each pad 36 and 38 is contained within a loosely knitted stocking or pocket 40 and 42, respectively, and the bags in turn are stitches as suggested at 44 and 46 to the inner surface 48 of sleeve 12. As shown in FIG. 4, the rows of stitching 44 securing the bag 40 to the inside of the sleeve are horizontal and lie at the top and bottom of the bag 40, while the rows of stitching 46 are essentially vertical and attach each side of the bag 42 to the inside 48 of sleeve 12.

As shown in FIGS. 1, 2, 4, and 9, pad 36 is generally elongated in a vertical (axial) direction and is somewhat wider at the top 50 than at the bottom 52 to resemble the outline of a human foot. It will be noted that the vertical, medial edge 54 of pad 36 is curved and lies closely adjacent the edge 32 of opening 30. In the embodiment shown, the edge 54 of the pad actually overlaps the edge 32 of the opening. The edge 54 is concave as viewed from the opening. The pad extends an appreciable distance both above and below the opening, and the edge 54 is designed to lie against the outside edge of the patella to prevent lateral displacement of the patella in the direction of the pad. While pad 36 is fairly rigid so as to prohibit lateral displacement of the patella, it is flexible enough so as not to prevent the leg from bending. Rather, it bends with the knee and stays in place. In FIGS. 9-11 pad 36 is shown provided with a ridge 70 formed on its outer surface 72 along the medial edge 54 and top edge 74 of the pad. The outer edge 56 of pad 36 essenticaly parallels and is adjacent to the stays 22 and 24 on the lateral side of the front portion 14 of the sleeve. The thinner lateral edge 56 of the pad is contoured to fit the leg. While the flange 70 is molded as an integral part of the pad and extends outwardly against the inner surface of the sleeve, it nevertheless increases the barrier formed by the pad against the side of the patella and prevents lateral displacement and upward drift of the patella. The elongated configuration of the pad follows the entire excursion of the patella during bending.

Condylar pad 38 which is designed to anchor the brace in place on the leg and prevent it from rotating, particularly as pressure is applied against the edge 54 of patella pad 36, is essentially oval in shape with the long axis arranged horizontally. The edge 60 of the pad 38 is substantially vertically aligned with the outer edge of opening 30 so that the pad when in place overlies the medial femoral epicondyl. A shallow cavity 62 and an enlarged ridge 63 are formed on the inner surface of the pad as shown in FIGS. 5-7. The enlarged ridge 63 engages the condyl notch 65 (see FIG. 12) while the cavity actually fits over the epicondyl 67. The contours of the pad and its location resist the tendency of the sleeve to rotate outwardly about its vertical axis and slip downwardly on the leg under the constant pressures applied to it by the patella bearing against pad 36. Thus, pad 38 serves as an anchor for the sleeve while the pad 36 performs its function of preventing lateral patella displacement.

Strap 80 on the sleeve extends laterally to medially over the front portion 14 and is made of an elastic webbing stretchable lengthwise but non-stretchable across its width. The lateral end 82 of the strap is stitched to the outer surface of the sleeve just beyond the lateral edge 75 of pad 36 and extends over the enlarged upper portion 50 of the pad and the upper portion of the patella opening 30. The free end 84 of strap 80 carries two spaced apart looped cotton strips 88 that serve as the female portion of a Velcro-type fastener. The strips 88 are stitched to the inner surface of the strap and are each designed to releasably lock onto the male Velcro-type patch 92 stitched over the medial stays 22 and 24. It will be appreciated that the user may pull the strap as tightly as desired to effectively reduce the brace diameter and apply pressure on the pads 36 and 38 so as to cause them to perform more effectively their respective functions as suggested by the arrows in FIG. 12. As the strap, when closed as shown in FIG. 2, overlies a substantial portion of pad 36, it applies pressure to the pad along its edge 54 and particularly to the flange 70 so as to create an effective barrier to prevent lateral displacement of the patella. It will also be noted in FIG. 2 that the strap covers a portion of the opening 30. Consequently, when the strap is pulled tight across the front of the sleeve as in FIG. 2, the strap prevents anterior displacement of the patella through the opening. In summary, the knee brace of this invention, unlike the prior art devices in combination provides a barrier against lateral displacement of the patella by the presence of pad 36, applies a pull on pad 36 through the strap 80, which in turn causes the pad to exert a medially directed force on the patella, and anchors the end of the strap to a fixed position on the knee by means of the condylar pad 38 and prevents anterior displacement of the patella by the position of the strap.

Having described this invention in detail, those skilled in the art will appreciate that numerous modifications may be made thereof without departing from the spirit of this invention. Therefore, it is not intended that the scope of the invention be limited to the specific embodiment illustrated and described. Rather, it is intended that the scope of the invention be determined by the appended claims and their equivalents.

What is claimed is:

1. A knee brace for preventing patella displacement comprising:
   a tubular sleeve made of an elastic webbing material, said sleeve being designed to fit over the leg and extend from below the knee upwardly to the thigh,
   a relatively firm elongated first pad attached to the sleeve, said pad being positioned on the sleeve to lie just laterally of the patella when the sleeve is worn on the leg overlying the knee so as to prevent lateral displacement of the patella when the sleeve is in place, and a second pad attached to the sleeve and positioned to engage the medial femoral epicondyl and condyl notch when the sleeve is in place and prevent the sleeve from turning on the leg and displace the first pad from the patella.

2. A knee brace as defined in claim 1 further characterized by a strap secured to the sleeve in the region of the first pad and extending medially over the sleeve, and fastening means secured to the sleeve in the region of the second pad for fastening the medial end of the strap so as to anchor the first pad to the second pad and pull the first pad against the patella.

3. A knee brace as defined in claim 2 further characterized by said first and second pads being attached to the inner surface of the sleeve.

4. A knee brace as defined in claim 3 further characterized by said pads being formed of a compliant material and contained within individual pockets attached to the inside of the sleeve.

5. A knee brace as defined in claim 2 further characterized by flexible stays secured to the sleeve and extending substantially the full length of the sleeve on each side thereof to prevent the sleeve from curling at its ends or twisting when the brace is on the leg.

6. A knee brace as defined in claim 2 further characterized by said sleeve being stretchable both in a circumferential and axial direction.

7. A knee brace as defined in claim 3 further characterized by said strap being stretchable lengthwise and said fastening means being a Velcro-type fastener.

8. A knee brace as defined in claim 1 further characterized by said first pad having an arcuate edge for facing the patella to prevent upward drift and lateral displacement of the patella.

9. A knee brace as defined in claim 8 further characterized by said first pad being elongated in a vertical direction generally parallel to the axis of the sleeve and having an enlarged upper portion which in part defines the arcuate edge.

10. A knee brace as defined in claim 9 further characterized by the arcuate edge being thicker than the remainder of the pad.

11. A knee brace as defined in claim 10 further characterized by a strap secured to the sleeve in the region of the first pad and extending medially over the sleeve, and fastening means secured to the sleeve in the region of the second pad for fastening the medial end of the strap causing the strap to pull the first pad against the patella.

12. A knee brace as defined in claim 11 further characterized by said second pad having a thickened portion adapted to fit into the condyle notch.

13. A knee brace as defined in claim 12 further characterized by a strap secured to the sleeve in the region of the first pad and extending medially over the sleeve, and fastening means secured to the sleeve in the region of the second pad for fastening the medial end of the strap causing the strap to pull the first pad against the patella.

14. A knee brace as defined in claim 1 further characterized by an adjustable strap secured to the sleeve in the vicinity of the first and second pads for tightening the sleeve about the knee region and anchoring the first pad to the second pad and pulling the first pad against the patella.

15. A knee brace as defined in claim 14 further characterized by said strap when tightened extending over the patella.

16. A knee brace for maintaining patella alignment comprising an elasticized tubular sleeve made of a two-way stretch material and sized to fit over the knee and extend from the calf to the thigh, a circular opening in the sleeve approximately midway between the top and bottom edges and positioned to expose the patella when the sleeve is worn on the leg, axially extending medial and lateral stays mounted in pockets provided in each side of the sleeve and positioned to lie against the inside and outside of the leg and prevent the sleeve from curling or twisting when worn, said stays permitting the sleeve to flex when the leg of the wearer is bent so as not to significantly interfere with leg mobility, a first pad attached to the inside of the sleeve laterally of the opening and between the opening and the outside stay, said pad being made of a stiff but yielding material and having an arcuate medial edge facing the opening and being concave with respect to the patella when the sleeve is worn, said pad preventing lateral displacement of the patella through the entire excursion of the patella when the knee is bent, a second pad attached to the inside of the sleeve above and medially of the opening and with its major portion lying between the opening and the inside stay, said second pad being generally oval in shape and made of a stiff but yielding material like the first pad, said pad having an enlargement on its inside surface and oriented to engage the medial femoral condyle notch and thereby prevent the sleeve from turning on the leg so as to maintain the brace in the proper position on the leg, a stretchable strap sewn at one end onto the sleeve and overlying the first pad and extending medially across the opening to the region of the second pad, and a Velcro-type fastener provided on the strap and on the other end of the strap and a Velcro-type fastener sewn to the outside of the sleeve over the second pad, said fasteners enable the user to pull the strap tightly in a medial direction and lock it in place so that the first pad will apply a force against the patella in a medial direction to prevent patella displacement to tighten the sleeve about the leg.

17. A knee brace as defined in claim 16 further characterized by said pads being made of a firm foam polystyrene, and a pocket containing each of the pads and stitched to the inside of the sleeve.

* * * * *